United States Patent [19]

Chen et al.

[11] Patent Number: 5,223,469
[45] Date of Patent: Jun. 29, 1993

[54] FLUIDIZED-BED CATALYST FOR PREPARING ACRYLONITRILE

[75] Inventors: Xin Chen; Lianghua Wu, both of Shanghai, China

[73] Assignee: China Petro-Chemical Corporation, Beijing, China

[21] Appl. No.: 786,217

[22] Filed: Oct. 31, 1991

[30] Foreign Application Priority Data

Nov. 5, 1990 [CN] China .................................. 90108811

[51] Int. Cl.$^5$ .......................... B01J 21/02; B01J 21/08; B01J 23/78; B01J 27/182
[52] U.S. Cl. .................................. 502/205; 502/209; 502/212; 502/241; 502/243; 558/324
[58] Field of Search ................ 558/324; 502/205, 209, 502/212, 241, 243

[56] References Cited

U.S. PATENT DOCUMENTS

| | | | |
|---|---|---|---|
| 4,162,234 | 7/1979 | Grasselli et al. | 502/212 X |
| 4,264,476 | 4/1981 | Umemura et al. | 502/241 X |
| 4,732,884 | 3/1988 | Sarumaru et al. | 502/205 |
| 4,981,830 | 1/1991 | Sasaki et al. | 502/209 X |
| 5,093,299 | 3/1992 | Suresh et al. | 502/212 |

Primary Examiner—W. J. Shine
Assistant Examiner—Douglas J. McGinty
Attorney, Agent, or Firm—Nikaido, Marmelstein, Murray & Oram

[57] ABSTRACT

The present invention relates to a fluidized-bed catalyst for propylene ammoxidation to produce acrylonitrile, which consists of silica support and a composite of the formula $$A_aB_bC_cNi_dCo_eNa_fFe_gBi_hM_iMo_jO_x$$

wherein A is potassium, rubidium, cesium samarium, thallium, or mixture thereof; B is manganese, magnesium, strontium, calcium, barium, lanthanum, rare earth, or mixture thereof; C is phosphorus, arsenic, boron, antimony, chromium, or mixture thereof; M is tungsten, vanadium, or mixture thereof. The catalyst of the present invention is highly active and selective for preparing acrylonitrile, more specifically, is suitable for catalyzing the reaction between air and propylene at a rather low ratio hence to greatly enlarge the processing capacity of the reactor. By using the catalyst of the present invention, the processing capacity of the reactor increases by 10-15 percent compared with that using conventional catalysts.

11 Claims, No Drawings

FLUIDIZED-BED CATALYST FOR PREPARING ACRYLONITRILE

FIELD OF THE INVENTION

The present invention relates to an ammoxidation catalyst, especially to a fluidized-bed catalyst for propylene ammoxidation to produce acrylonitrile.

BACKGROUND OF THE INVENTION

Mo-Bi-Fe catalyst series is known as an oxidation catalyst series. The performance of this kind of catalyst such as activity and selectivity is not very satisfactory. Chinese Patent 87103455.7 and U.S. Pat. No. 4,162,234 disclosed a catalyst, in which alkali metals such as Na, K, Rb, Cs, etc. were added to improve the activity and abrasion-resistance of the catalyst. Only one alkali metal element was incorporated into the above-mentioned catalysts. Japanese Patent No. 58-2232 (corresponding to U.S. Pat. No. 4,228,098) and Chinese Patent 86101301 disclosed a fluidized-bed catalyst for preparing acrylonitrile, in which a part of molybdenum component was replaced by tungsten component to improve the catalyst selectivity for acrylonitrile. The improvement in the activity and selectivity of the disclosed catalysts for preparing acrylonitrile is not significant and the processing capacity of the reactor is still limited.

OBJECTS OF THE INVENTION

The purpose of the present invention is to provide a fluidized-bed catalyst for preparing acrylonitrile, possessing high activity and selectivity and being able to enlarge the processing capacity of the reactor.

Comparing with the catalysts of prior art in the same category, the advantages of the catalyst of the present invention are significant, which will be described in detail hereinafter.

SUMMARY OF THE INVENTION

The fluidized-bed catalyst for preparing acrylonitrile of the present invention comprises silica support and a composite of the formula $$A_aB_bC_cNi_dCo_eNa_fFe_gBi_hM_iMo_jO_x$$

wherein
A is potassium, rubidium, cesium, samarium, thallium, or mixture thereof;
B is manganese, magnesium, strontium, calcium, barium, lanthanum, rare earth other than samarium, or mixture thereof;
C is phosphorus, arsenic, boron, antimony, chromium, or mixture thereof;
M is tungsten, vanadium, or mixture thereof;
and
a is in the range of 0.01–1;
b is in the range of 0.1–3;
c is in the range of 0.01–2;
d is in the range of 0.01–8;
e is in the range of 0.01–12;
f is in the range of 0.2–0.7;
g is in the range of 0.01–8;
h is in the range of 0.01–6;
i is in the range of 0.01–6;
j is in the range of 6–11.99;
x is the number of oxygen atoms required for balancing the valence state of the other elements presented in the catalyst;
i+j constantly equals 12;
and, the content of silica support in the catalyst is in the range of 30–70 percent by weight.

DETAILED DESCRIPTION OF THE INVENTION

The present invention relates to an ammoxidation catalyst, especially relates to a fluidized-bed catalyst for preparing acrylonitrile.

The catalyst of the present invention is a Mo-Bi oxidation catalyst, in which sodium is contained; molybdenum is partly replaced by tungsten, vanadium, or mixture thereof, to improve the catalyst selectivity to acrylonitrile; potassium, rubidium, cesium, samarium, thallium or mixture of at least three elements thereof is incorporated into the catalyst to further enhance is activity; silicon dioxide is selected as the support of the catalyst of the present invention. The precursor of the silica support may be ammonia-stabilized sodium-free silica sol, in which the content of silica is 40 percent by weight.

The active composite of the catalyst of the present invention is a composite of the formula $$A_aB_bC_cNi_dCo_eNa_fFe_gBi_hM_iMo_jO_x$$

wherein
A is potassium, rubidium, cesium, samarium, thallium, or mixture thereof;
B is manganese, magnesium, strontium, calcium, barium, lanthanum, rare earth other than samarium, or mixture thereof;
C is phosphorus, arsenic, boron, antimony, chromium, or mixture thereof;
and
a is in the range of 0.01–1, preferably in the range of 0.03–0.4;
b is in the range of 0.1–3, preferably in the range of 0.5–2;
c is in the range of 0.01–2, preferably in the range of 0.1–1.5;
d is in the range of 0.01–8, preferably in the range of 0.5–5;
e is in the range of 0.01–12, preferably in the range of 0.5–8;
f is in the range of 0.2–0.7, preferably in the range of 0.3–0.5;
g is in the range of 0.01–8, preferably in the range of 0.1–4;
h is in the range of 0.01–6, preferably in the range of 0.1–4;
i is in the range of 0.01–6, preferably in the range of 0.01–3;
j is in the range of 6–11.99, preferably in the range of 9–11.90;
x is the number of oxygen atoms required for balancing the total valence state of the other elements presented in the catalyst;
i+j constantly equals 12; and the content of silica support is in the range of 30–70 percent by weight, preferably in the range of 40–60 percent by weight.

In the catalyst of the present invention, molybdenum component is partly replaced by tungsten, vanadium, or mixture thereof, to improve the catalyst selectivity to acrylonitrile. The amount of tungsten, vanadium, or mixture thereof introduced into the catalyst of the present invention must be in a certain range. Below this range, the performance of the catalyst can not be improved; beyond this range the activity of the catalyst will be depressed. Usually, the value of i is selected in the range of 0.01-6. When M is tungsten, i is preferably in the range of 0.1-3; when M is vanadium, i is preferably in the range of 0.1-3.

The element A is the catalyst of the present invention is potassium, rubidium, cesium, samarium, thallium, or mixture thereof, which can significantly enhance the activity of the catalyst. Preferably, A is a mixture of at least three elements selected from the above-mentioned five elements, for example, the mixture of potassium, rubidium, and cesium; the mixture of cesium, samarium, and thallium; the mixture of rubidium, cesium, and samarium, or the mixture of potassium, cesium, and thallium.

The catalyst of the present invention can be prepared by conventional methods; catalyst components, support, and water are firstly mixed to form paste, followed by spray drying to form microspheres, and calcining to obtain catalyst product.

The raw materials selected for preparing the catalyst of the present invention are as follows.

Element A preferably originates from its nitrates, hydroxides, or salts which are decomposible to oxides.

Element B can originate from its oxides or salts which are decomposible to oxides. In the group of element C, phosphorus, arsenic, and boron preferably originate from their corresponding acids or ammonium salts; chromium preferably originates from chromium trioxide (the valence state of chromium is 6), chromium nitrate, or their mixture; antimony can originate from tri-valence state oxide ($Sb_2O_3$), penta-valence state oxide ($Sb_2O_5$), chlorides or antimony sol which can be hydrolyzed to antimony oxides.

Sodium component can be selected from sodium nitrate, sodium hydroxide, sodium silicate, or any sodium compound which can be decomposible to oxide.

Components nickel, cobalt, iron, and bismuth can be selected from their oxides or their salts which are decomposible to oxides, the preferable salts are water-soluble nitrates.

About element M, tungsten can originate from tungsten oxide, vanadium can originate from ammonium metavanadate.

Molybdenum component can be selected from molybdenum oxide or ammonium molybdate.

The raw material for silica support can be ammonium-stabilized sodium-free silica sol, in which the content of silica is 40 percent by weight.

After heat-treatment, the prepared slurry is spray-dried for shaping. The spray-drier can be pressure-type, double-stream type, or centrifugal rotating-disc type, preferably the centrifugal rotating disc type which can attain a suitable particle-size distribution for catalyst product.

The calcination of the catalyst can be divided into two stages, e.g. the decomposition of the salts of various elements in the catalyst and the high temperature calcination. During the decomposition stage, the temperature should be controlled in the range of 200°-400° C. and the decomposition lasts for about 0.5 to about 2 hours. The calcination temperature is in the range of 500°-800° C., preferably in the range of 550°-650° C. The decomposition and calcination can be performed in separate ovens, or in same oven by two temperature stages, or simultaneously in a continuous rotating oven. A suitable amount of flowing air is needed in the oven for the catalyst decomposition and calcination processes.

The specifications of propylene, ammonia, and oxygen required for preparing acrylonitrile using the catalyst of the present invention are the same as that using other catalysts. Although the content of alkanes of low molecular weight in propylene has no influence on reaction, the concentration of propylene should be higher than 85 percent by mole from economic viewpoint. Ammonia used can be a fertilizer-grade liquid ammonia. Technologically, pure oxygen or oxygen-riched air is preferred for reaction, however, it is more reasonable to use air as oxygen source from the viewpoint of economy and resource availability.

The mole ratio of ammonium to propylene feeding to the fluidized-bed reactor can be varied from 0.8:1 to 1.5:1, preferably from 1.0:1 to 1.3:1. The actual mole ratio of air to propylene is preferably between 8:1 and 10:1. Such a low ratio shows the important advantage in the application of the catalyst of the present invention. Higher air ratio such as 11:1 may be adopted by some reason without significant unfavorable effect on reaction. However, for the reason of safety, the volume content of oxygen in the gaseous reactant should not be higher than 7 percent by volume, preferably not higher than 4 percent.

When the catalyst of the present invention is used in a fluidized-bed reactor, the reaction temperature is in the range of 420°-490° C., preferably in the range of 440°-460° C., the pressure is usually in the range of 0.01-0.2 MPa, preferably in the range of 0.04-0.2 MPa.

The weight of propylene feed per unit weight of catalyst per hour (WWH) is in the range of 0.04-0.20, preferably in the range of 0.05-0.10.

The definition of WWH is

WWH = weight of propylene feed/weight of catalyst . hr.

The product recovery and refining technology for preparing acrylonitrile using the catalyst of the present invention is the same as that of the conventional technology. The un-reacted ammonia in the effluent from the fluidized-bed reactor is removed in a neutralization tower, all the organic components are absorbed in an absorption tower by water. Extractive distillation is used for removing hydrogen cyanide and water from the absorbed liquid to obtain high purity acrylonitrile product.

The detailed description combined with the embodiments of the present invention will be given below. The definitions of propylene conversion, acrylonitrile selectivity, and single pass yield are respectively:

$$\frac{\text{propylene}}{\text{conversion (\%)}} = \frac{\text{moles of propylene being converted}}{\text{moles of propylene being feeded}} \times 100$$

$$\frac{\text{acrylonitrile}}{\text{selectivity (\%)}} = \frac{\text{moles of acrylonitrile produced}}{\text{moles of propylene being converted}} \times 100$$

$$\frac{\text{acrylonitrile}}{\text{single-pass}} = \frac{\text{moles of acrylonitrile produced}}{\text{moles of propylene being feeded}} \times 100$$
$$\text{yield (\%)}$$

EXAMPLE 1

Material (I) was prepared by mixing 20 percent by weight potassium nitrate solution 9.2 g, 20 percent by weight rubidium nitrate solution 13.4 g, 20 percent by weight cesium nitrate solution 8.9 g, and 20 percent by weight sodium nitrate solution 23.2 g.

Material (II) was prepared by dissolving 23.7 g ammonium tungstate in 100 ml 5 percent by weight ammonia water followed by mixing with a solution of 368.3 g ammonium molybdate in 300 ml hot water of a temperature ranging 50°–95° C.

Material (III) was prepared by dissolving a mixture of 79.2 g bismuth nitrate, 52.1 g manganese nitrate, 131.9 g iron nitrate, 211.1 g cobalt nitrate, 121.3 g nickel nitrate, and 29.0 g chromium nitrate in 70 ml water by heating.

Material (I) was mixed with 40 percent by weight ammonia-stabilized sodium-free silica sol 1250 g, to which 85 percent by weight phosphoric acid 5.23 g, materials (II) and (III) were added while stirring. After thoroughly stirring, a paste was formed, which was spray-dried according to conventional method to obtain microspheres followed by calcining at 670° C. for 1 hour. in a rotating oven with a inner-diameter of 89 mm and a length of 1700 mm ($\phi 89 \times 1700$ mm). The prepared catalyst had a composition as follows:

$$Mo_{11.5}W_{0.5}Bi_{0.9}Fe_{1.8}Co_{4.0}Ni_{2.3}Mn_{1.0}Cr_{0.4}P_{0.25}Na_{0.3}K_{0.1}Rb_{0.1}Cs_{0.05}O_x + 50\% SiO_2.$$

The catalyst was evaluated in a fluidized-bed reactor having a inner-diameter of 38 mm. The reaction temperature was 435, pressure was 0.08 MPa, mole ratio of propylene:ammonia:air = 1:1.2:9.2, and WWH was 0.045. The results were:
propylene conversion 96.2%
acrylonitrile selectivity 83.3%
acrylonitrile single-pass yield 80.1%.

When the feeding rate of propylene at the above-mentioned ratio was 245 ml/min, the amount of acrylonitrile produced was $$(245/22.4) \times 0.801 \times 53 = 464.3 \text{ g/min.}$$

When the mole ratio of the raw materials was changed to propylene:ammonia:air = 1:1.5:10.5 meanwhile other operation parameters remained unchanged, the evaluation results were:
propylene conversion 97.8%
acrylonitrile selectivity 81.0%
acrylonitrile single-pass yield 79.2%.

When the feeding rate of propylene at this ratio was 219 ml/min, the amount of acrylonitrile produced was $$(219/22.4) \times 0.792 \times 53 = 410 \text{ g/min}$$

EXAMPLE 2

The catalyst was prepared by the process described in Example 1. Material (I) was prepared by mixing a series of 20 percent by weight solutions including 15.6 g rubidium nitrate solution, 10.4 g cesium nitrate solution, 47.4 g samarium nitrate solution, and 27.2 g sodium nitrate solution.

Material (II) was prepared by mixing a solution of 55.7 g ammonium tungstate in 300 ml 5 percent by weight ammonia water with another solution of 414.2 g ammonium molybdate in 350 ml hot water of a temperature ranging 50°–95° C.

Material (III) was prepared by mixing 93.1 g bismuth nitrate, 155.1 g iron nitrate, 61.2 g manganese nitrate, 248.3 g cobalt nitrate, 142.6 g nickel nitrate, 34.1 g chromium nitrate, and 100 ml water.

According to the process described in Example 1, above materials were mixed with 1000 g 40 percent by weight silica sol and 6.15 g 85 percent by weight phosphoric acid, after shaping and calcining, the catalyst obtained had a composition as follows:

$$Mo_{11.0}W_{1.0}Bi_{0.9}Fe_{1.8}Co_{4.0}Ni_{2.3}Mn_{1.0}Cr_{0.4}P_{0.25}Rb_{0.1}Cs_{0.1}Sm_{0.1}Na_{0.3}O_x + 40\% SiO_2.$$

The evaluation method for catalyst activity was the same as that of Example 1. The operation parameters were also the same as that of Example 1 except the mole ratio of propylene:ammonia:air = 1:1.2:9.4, The results were:
propylene conversion—98.5%
acrylonitrile selectivity—83.1%
acrylonitrile single-pass yield—81.9%

EXAMPLE 3

The catalyst was prepared by the process described in Example 1. Material (I) was prepared by mixing a series of 20 percent by weight solutions including 9.3 g potassium nitrate solution, 8.9 g cesium nitrate solution, 24.3 g thallium nitrite solution, and 23.3 g sodium nitrate solution.

Material (II) was prepared by mixing a solution of 9.5 g ammonium tungstate in 50 ml 5 percent by weight ammonia water with another solution of 380.1 g ammonium molybdate in 300 ml hot water of a temperature ranging 50°–95° C.

Material (III) was prepared by mixing 79.7 g bismuth nitrate, 132.7 g iron nitrate, 212.4 g cobalt nitrate, 122.0 g nickel nitrate, 52.4 g manganese nitrate, 29.2 g chromium nitrate and 70 ml water.

According to the process described in Example 1, above materials were mixed with 1250 g 40 percent by weight silica sol, 3.16 g 85 percent by weight phosphoric acid, and a solution of 1.13 g boric acid, after shaping and calcining, the catalyst obtained had a composition as follows:

$$Mo_{11.8}W_{0.2}Bi_{0.9}Fe_{1.8}Co_{4.0}Ni_{2.3}Mn_{1.0}Cr_{0.4}P_{0.15}B_{0.1}Na_{0.3}K_{0.1}Cs_{0.05}Tl_{0.1}O_x + 50\% SiO_2.$$

The evaluation method for catalyst activity was the same as that of Example 1. The operation parameters were also the same as those of Example 1 except the mole ratio of propylene:ammonia:air = 1:1:8.9. The results were:
propylene conversion 96.1%
acrylonitrile selectivity 82.9%
acrylonitrile single-pass yield 79.7%

EXAMPLE 4

The catalyst was prepared by the process described in Example 1. Material (I) was prepared by mixing a series of 20 percent by weight solution including 9.0 g cesium nitrate solution, 41.0 g samarium nitrate solution, 24.6 g thallium nitrite solution, and 23.5 g sodium nitrate solution.

Material (II) was prepared by mixing a solution of 24.1 g ammonium tungstate in 100 ml 5 percent by weight ammonia water with another solution of 374.1 g ammonium molybdate in 300 ml hot water of a temperature ranging 50°–95° C.

Material (III) was process described by mixing 80.4 g bismuth nitrate, 134.04 g iron nitrate, 52.9 g manganese nitrate, 94.5 g magnesium nitrate, 107.2 g cobalt nitrate, 123.2 g nickel nitrate, 29.5 g chromium nitrate, and 70 ml water.

According to the process described in Example 1, above materials were mixed with 1250 g 40 percent by weight silica sol and 5.31 g 85 percent by weight phosphoric acid, after shaping and calcining, the catalyst obtained had a composition as follows:

$Mo_{11.5}W_{0.5}Bi_{0.9}Fe_{1.8}Co_{2.0}Mg_{2.0}Ni_{2.3}Mn_{1.0}Cr_{0.4}P_{0.25}Cs_{0.05}Sm_{0.1}Tl_{0.1}Na_{0.3}O_x + 50\%SiO_2$.

The evaluation method for catalyst activity was the same as that of Example 1. The operation parameters were the same as those of Example 1, except the mole ratio of propylene:ammonia:air = 1:1.15:9.5. The results were:
propylene conversion 95.5%
acrylonitrile selectivity 81.5%
acrylonitrile single-pass yield 78.9%

EXAMPLE 5

The catalyst was prepared by the process described in Example 1. Material (I) was prepared by mixing a series of 20 percent by weight solutions including 22.1 g sodium nitrate solution, 17.5 g potassium nitrate solution, and 8.5 g cesium nitrate solution.

Material (II) was prepared by dissolving 4.05 g ammonium metavanadate and 361.0 g ammonium molybdate in 300 ml hot water of a temperature ranging 50°–90° C.

Material (III) was prepared by mixing 84.1 g bismuth nitrate, 140.0 g iron nitrate, 75.2 g cerium nitrite, 242.0 g cobalt nitrate, 74.6 g mangeanese nitrate, 18.7 g chramium nitrate, 11.54 g thallium nitrate and 100 ml water.

According to the process described in Example 1, above materials were mixed with 1250 g 40 percent by weight silica sol and 16.1 g boric acid, after shaping and calcination, the catalyst obtained had a composition as follows:

$Mo_{11.8}V_{0.2}Bi_{1.0}Fe_{2.0}Ce_{1.0}Co_{4.8}Mn_{1.5}Cr_{0.27}Na_{0.3}K_{0.2}Tl_{0.25}Cs_{0.05}B_{1.5}O_x + 50\%SiO_2$.

The catalyst evaluation method was the same as that of Example 1. The operation parameters were the same as those of Example 1 except the mole ratio of propylene:ammonia:air = 1:1.1:9.4. The results were:
propylene conversion 97.8%
acrylonitrile selectivity 81.5%
acrylonitrile single-pass yield 79.7%

EXAMPLE 6

The catalyst was prepared by the process described in Example 1. Material (I) was prepared by mixing a series of 20 percent by weight solutions including 21.6 g sodium nitrate solution, 8.6 g potassium nitrate solution, 12.15 g rubidium nitrate solution, and 8.3 g cesium nitrate solution.

Material (II) is prepared by mixing 82.2 g bismuth nitrate, 136.9 g iron nitrate, 110.1 g lanthanum nitrate, 98.7 g cobalt nitrate, 98.6 g nickel nitrate, 73.0 g manganese nitrate, 20.3 chromium nitrate, and 80 ml water.

Material (III) was prepared by dissolving 314.3 g ammonium molybdate, 66.4 g ammonium tungstate, and 5.95 g ammonium melavanadate, in 300 ml 5 percent by weight hot ammonia water of a temperature ranging 50°–95° C.

According to the process described in Example 1, above materials were mixed with 9.8 g 85 percent by weight phosphoric acid and 1250 g 40 percent by weight silica sol, after shaping and calcination, the catalyst obtained had a composition as follows:

$Mo_{10.5}W_{1.2}V_{0.3}Bi_{1.0}Fe_{2.0}La_{1.5}Co_{2.0}Ni_{2.0}Mn_{1.5}Cr_{0.3}Na_{0.3}K_{0.1}Rb_{0.1}Cs_{0.05}P_{0.5}O_x + 50\%SiO_2$.

The evaluation method for catalyst activity was the same as that of Example 1. The operation parameters were the same as those of Example 1 except the mole ratio of propylene:ammonia:air = 1:1.15:9.1. The results were:
propylene conversion 94.5%
acrylonitrile selectivity 84.1%
acrylonitrile single-pass yield 79.5%

EXAMPLE 7

Material (I) was prepared by mixing a series of 20 percent by water solutions including 8.9 g cesium nitrate solution, 23.35 g sodium nitrate solution, 22.7 g potassium nitrate solution, 21.2 g rubidium nitrate solution, and 25.5 g samarium nitrate solution.

Material (II) was prepared by mixing a solution of 10.8 g ammonium tungstate in 70 ml 5 percent by weight ammonia water with another solution of 373.4 g ammonium molybdate in 330 ml hot water of a temperature ranging 50°–95° C.

Material (III) was prepared by dissolving 80.29 g bismuth nitrate, 214.1 g cobalt nitrate, 124.3 g nickel nitrate, 135.1 g iron nitrate, 65.2 g manganese nitrate, and 5.6 g chromium nitrate, in 65 ml water by heating.

Material (I) prepared was mixed with 1250 g 40 percent by weight ammonia-stabilized sodium-free silica sol, followed by adding to it materials (II) and (III) while stirring. The obtained mixture was heated at 80° C. for 5 hours to form catalyst paste, which was spray-dried by conventional method for shaping, heated at 250° C. for 10 hrs, finally calcined at 660° C. in a rotating calcination oven for 1 hour to obtain the catalyst with a composition of:

$Mo_{11.5}W_{0.5}Bi_{0.9}Fe_{1.8}Co_{4.0}Ni_{2.3}Mn_{1.0}Cr_{0.3}Na_{0.3}K_{0.2}Cs_{0.05}Rb_{0.1}Sm_{0.1}O_x + 50\%SiO_2$.

The evaluation method for catalyst activity was the same as that of Example 1. The results were:
propylene conversion 98.7%
acrylonitrile selectivity 82.8%
acrylonitrile single-pass yield 81.7%

EXAMPLE 8

The catalyst was prepared by the process described in Example 1. Material (I) was prepared by mixing 13.97 g thallium nitrite, 4.43 g sodium nitrate, 2.16 g potassium nitrate, 4.02 g rubidium nitrate, and 100 ml water.

Material (II) was prepared by mixing 84.8 g bismuth nitrate, 118.1 g nickel nitrate, 74.31 g manganese nitrate, 8.8 g chromium nitrate, and 70 ml water.

Material (III) was prepared by dissolving 339.4 g ammonium molybdate, 33.0 g ammonium tungstate, and 6.20 g ammonium metavanadate, in 300 ml 5 percent by weight hot ammonia water of a temperature ranging 50°–95° C.

According to the process described in Example 1, above materials were mixed with 1250 g 40 percent by weight ammonia-stabilized sodium free silica sol and 100 ml solution of 10.8 g boric acid in water, after shaping and calcination, the catalyst obtained had a composition as follows:

$$Mo_{11.0}W_{0.7}V_{0.3}Bi_{1.0}Fe_{2.0}Co_{4.0}Ni_{2.3}Mn_{1.2}Cr_{0.5}Na_{0.3}Tl_{0.3}B_{1.0}K_{0.1}Rb_{0.1}O_x + 50\%SiO_2.$$

The evaluation method for catalyst activity was the same as that of Example 1. The operation parameters were the same as those of Example 1, except the mole ratio of propylene:ammonia:air=1:1.5:9.0. The results were:
propylene conversion 98.9%
acrylonitrile selectivity 81.7%
acrylonitrile single-pass yield 80.8%

EXAMPLE 9

The catalyst preparation and activity evaluation were the same as those of Example 7, except that thallium was used to replace cesium and phosphorus was further added. The catalyst obtained had a composition as follows:

$$Mo_{11.0}W_{1.0}B_{1.0}Fe_{2.0}Co_{4.0}Ni_{2.0}Mn_{1.0}Na_{0.3}Cr_{0.2}P_{0.25}Rb_{0.05}Tl_{0.05}Sm_{0.1}K_{0.5}O_x + 50\%SiO_2.$$

The evaluation results of catalyst activity were as follows:
propylene conversion 97.8%
acrylonitrile selectivity 83.0%
acrylonitrile single-ass yield 81.2%

EXAMPLE 10

The catalyst preparation and activity evaluation were the same as that of Example 8, except that antimony was used to replace vanadium and cesium was used to replaced rubidium. The catalyst obtained had a composition as follows:

$$Mo_{11.2}W_{0.8}Bi_{1.0}Fe_{2.0}Co_{0.4}Ni_{2.0}Mn_{1.0}Cr_{0.2}Sb_{0.2}B_{1.5}Tl_{0.05}Cs_{0.05}K_{0.1}Na_{0.3}O_x + 50\%SiO_2.$$

The evaluation results of catalyst activity were as follows:
propylene conversion 97.0%
acrylonitrile selectivity 82.4%
acrylonitrile single-pass yield 79.9%.

What we claim is:

1. A fluidized-bed catalyst for preparing acrylonitrile comprising silica support and a composite of the formula $$A_aB_bC_cNi_dCo_eNa_fFe_gBi_hM_iMo_jO_x$$

wherein
A is potassium, rubidium, cesium, samarium, thallium, or mixture thereof;
B is manganese, magnesium, strontium, calcium, barium, lanthanum, rare earth other than samarium or mixture thereof;
C is phosphorus, arsenic, boron, antimony, chromium, or mixture thereof;
M is tungsten, vanadium, or mixture thereof; and
a is in the range of 0.01–1;
b is in the range of 0.1–3;
c is in the range of 0.01–2;
d is in the range of 0.01–8
e is in the range of 0.01–12;
f is in the range of 0.2–0.7;
g is in the range of 0.01–8;
h is in the range of 0.01–6;
i is in the range of 0.01–6;
j is in the range of 6–11.99;
x is the number of oxygen atoms required for balancing the valence state of the other elements presented in the catalyst;
i+j constantly equals 12; and
the content of silica support in the catalyst is in the range of 30–70 percent by weight.

2. The catalyst of claim 1, wherein A is a mixture of at least three elements from potassium, rubidium, cesium, samarium, and thallium.

3. The catalyst of claim 2, wherein A is the mixture of potassium, rubidium, and cesium.

4. The catalyst of claim 2, wherein A is the mixture of cesium, samarium, and thallium.

5. The catalyst of claim 2, wherein A is the mixture of rubidium, cesium, and samarium.

6. The catalyst of claim 2, wherein A is the mixture of potassium, cesium, and thallium.

7. The catalyst of claim 1, wherein M is tungsten.

8. The catalyst of claim 1, wherein M is vanadium.

9. The catalyst of claim 1, wherein M is the mixture of tungsten and vanadium.

10. The catalyst of claim 1, wherein
a is in the range of 0.03–0.4;
b is in the range of 0.5–2;
c is in the range of 0.1–1.5;
d is in the range of 0.5–5;
e is in the range of 0.5–8;
f is in the range of 0.3–0.5;
g is in the range of 0.1–4;
h is in the range of 0.1–4;
i is in the range of 0.1–3;
j is in the range of 9–11.90;
x is the number of oxygen atoms required for balancing the valence state of the other elements presented in the catalyst; and
i+j constantly equals 12.

11. The catalyst of claim 1, wherein the content of silica support in the catalyst is in the range of 40–60 percent by weight.

* * * * *